United States Patent [19]

Hayashi et al.

[11] Patent Number: 4,858,560

[45] Date of Patent: Aug. 22, 1989

[54] METHOD OF BREEDING POULTRY FOR FOOD

[75] Inventors: Kunioki Hayashi, Kagoshima; Hironori Tanaka, Yokohama; Tsutomu Sasagawa, Shizuoka; Isao Uemura, Kasukabe; Akira Aizawa, Ohamishirasato, all of Japan

[73] Assignees: Toyo Jozo Co., Ltd., Shizuoka; Ise Chemical Industries Co., Ltd., Tokyo, both of Japan

[21] Appl. No.: 137,809

[22] Filed: Dec. 24, 1987

[51] Int. Cl.$^4$ ............................................. A61K 33/18
[52] U.S. Cl. ....................................... 119/1; 424/668; 424/671
[58] Field of Search ................. 424/150; 426/2; 119/1

[56] References Cited

U.S. PATENT DOCUMENTS

| | | | |
|---|---|---|---|
| 4,087,554 | 5/1978 | Haydock et al. | 514/721 X |
| 4,187,294 | 2/1980 | Ishikawa et al. | 424/150 |
| 4,485,098 | 11/1984 | Sekimoto et al. | 424/105 |

FOREIGN PATENT DOCUMENTS

| | | | |
|---|---|---|---|
| 1158983 | 12/1983 | Canada | 424/150 |
| 35882 | 9/1981 | European Pat. Off. | 424/150 |

*Primary Examiner*—Robert P. Swiatek
*Attorney, Agent, or Firm*—Oblon, Spivak, McClelland, Maier & Neustadt

[57] ABSTRACT

Method of breeding poultry for food wherein they are fed with specific feedstuff, particularly at their age of from 10 to 60 days, in order to improve the meat quality so that they have meager fat and much meat in the body; the feedstuff contains either protein which contains both iodide (i.e. sodium iodide) and iodate (i.e. sodium iodate) in combination, or protein with which iodine is combined; the ratio of the iodide-and-iodate-containing protein to the feedstuff is from 1 to 3500 ppm, and the ratio of iodine-combined protein to the feedstuff is from 1 to 350 ppm, respectively as iodine concentration.

3 Claims, No Drawings

METHOD OF BREEDING POULTRY FOR FOOD

BACKGROUND OF THE INVENTION

1. Field of the Invention

The present invention relates to a method of breeding poultry for food, it relates more particularly to a method of breeding such poultry for food as broilers and the like, characterized in that a specific iodine-containing protein is fed to the poultry in a certain period of time for breeding, thereby to lessen the body-fat and develop muscles in their body.

2. Description of the Prior Art

Referring to poultry for food, particularly broilers, generally when they have been fed for about 60 days after hatching (namely when they have reached the age of 60 days), they are to be shipped to the market. And since poultry that have meager fat and much meat are appreciated as good qualities in the market, various measures have been taken up to this time for the purpose of breeding up such poultry for food as may satisfy the above conditions.

As a method of breeding up poultry to be fleshy, that is, to have increased body-weight, addition of antibiotics or synthetic antifungus agents to the feedstuff is generally practiced, and further addition of hormone drugs is also attempted. However, antibiotics and hormone drugs are not only costly, but also they will produce a considerable effect also upon human bodies, for that reason, the use of antibiotics and hormone drugs are placed under strict regulations by the authorities, and particularly addition of hormone drugs to the feedstuff is not always so easily permitted.

On the other hand, as iodine-type additives to the feedstuff, potassium iodide, potassium iodate and calcium iodate are permitted to be employed; indeed such inorganic iodine may be effective in the treatment of the iodine-deficiency disease, but they have no effect in accelerating growth of the poultry.

It is disclosed in Japanese Patent Publication No. 48-1483, and No. 49-46752 that iodocasein has an effect of thyroxine, and that the hydrolysate of iodocasein has an effect of increasing body weight of animals, but those additives have not been put to the practical use. It is because that the general term "iodocasein" includes various kinds of iodocasein, and they have respectively different contents of iodine, and that a certain kind of iodocasein will induce decrease, instead of increase, in the body weight of the poultry, and that it has sometimes no effect at all on the poultry depending upon the age of the poultry to be fed with the feedstuff containing such additives.

SUMMARY OF THE INVENTION

Under such conditions, the present inventors continued their assiduous studies, and found a specific method of breeding poultry, in which poultry can be bred up to have meager fat and increased muscles in the body by feeding them with the feedstuff containing a specific iodinecontaining protein in a certain period for their breeding, and they have brought the finding to the accomplishment of the present invention.

DETAILED DESCRIPTION OF THE PREFERRED EMBODIMENTS

Thus the present invention provides a method of breeding poultry for food characterized by feeding the poultry at the age of from 10 to 60 days with a feedstuff which contains a protein containing both iodine and iodate, or a protein combined with iodine.

As iodides in the present invention may be mentioned, potassium iodide, sodium iodide, cuprous iodide, calcium iodide etc., but among them potassium iodide is particularly preferable. And as iodates may be mentioned, potassium iodate, sodium iodate, calcium iodate, but among them potassium iodate is particularly preferable. On the other hand as protein, if it is sparingly soluble in water, and it can be combined with iodine, any kind thereof will do, and as such can be mentioned, for example, vegetable protein of soybean, corn etc., and animal protein of fish meal, serum, albumen, milk etc., but among them milk, particularly milkcasein is preferable in view of its property of combining with iodine, and its economical merits.

In the present invention, the iodine compound contained in the protein should be, as an essential condition, a blend of both iodide and iodate in a combined form, and if the compound lacks any one of them, the object of the present invention will not be attained. The ratio of iodide to iodate is preferably 1 to 10 parts by weight of iodide to 1 part by weight of iodate. The blending ratio of iodide and iodate to the protein is preferably about 10 wt % (hereinafter indicated simply as %) in the total iodine-amount to the whole. Further it is preferable that the above specific protein which contains iodide and iodate is to be so formulated that the iodine concentration in the feedstuff will be from 1 to 3500 ppm.

The iodine-combined protein may be prepared by the well-known process, that is, for example, if either iodine or iodine-compound is added to an aqueous solution of protein to be reacted with each other, generally 1 to 10% of iodine-combined protein, as combined-iodine amount, can be obtained. It is preferable that such iodine-combined protein is so formulated that the iodine concentration in the feedstuff will be from 1 to 350 ppm.

Besides the above mentioned iodine-containing protein, the below mentioned generally used additives may also be blended, in an appropriate combination thereof, with the feedstuff in the present invention. Examples of such additives include vitamins such as A, $B_1$, $B_2$, $B_6$, $B_{12}$, C, $D_2$, E, $K_3$, coline, panthothenic acid, biotin, nicotinic acid, inositol etc.; minerals, such as K, Na, Ca, P, Mg, Fe, Zn, Mn, Co, Se, etc.; amino acids such as methionine, lysine, tryptophan, glutamic acid, glycine, alanine etc.; antibiotics of types of macrolide, tetracycline, polypeptide, polysacchride, and polyether; and further, synthetic antifungus agents, synthetic anti-coccidiosis agents, vermicides, enzyme agents, antioxidants, binding agents, emulsifying agents, antifungal agents, seasoning agents, coloring agents and the like.

In the present invention, the feedstuff, formulated as above, is required to be fed to the poultry for food at the age of 10 to 60 days, particularly preferably at the age of 30 to 50 days.

Action and effect

It can be assumed that the decrease in the fat and the development of the muscle in the poultry body may depend upon activation of the thyroid function caused by the iodine-combined protein. And further it can be imagined that in the case of feedstuff containing the protein that contains iodide and iodate, the following reaction, for example, $KIO_3 + 5KI + 6HCl$ (gastric acid) $\rightarrow 3I_2 + 6KCl + 3H_2O$, will occur in the digestive tract to produce free iodine ($I_2$), which combines with protein to be iodine-combined protein, and exerts the effect.

EXAMPLES

The present invention will be explained below referring to the embodiments described below.

EXAMPLE 1

Process for the preparation 1

100 g of milkcasein was suspended in 2 l of water, then 10 g of powdered iodine was added to the suspension. After stirring, the liquor was allowed to stand at room temperature for 24 hours. Further through processes of dehydration, drying, and grinding, iodine-containing milkcasein was obtained.

Process for the preparation 2

Iodine-containing milkcasein was obtained through the process similar to the Process 1, except that 15 g of powdered iodine was employed in this process.

Process for the preparation 3

Iodine-containing milkcasein was obtained through the process similar to the Process 1, except that 25 g of powdered iodine was employed.

Process for the preparation 4

100 g of milkcasein was dissolved in 2 l of aqueous solution of sodium bicarbonate (7 g/l), to the solution was added dropwise, over a period of 1 hour, a solution of 10 g of iodine in 75 ml of ethyl alcohol, and it was stirred. 15 ml of 10% sulfuric acid was added thereto to adjust the pH value to the vicinity of pH 4.8, and iodine-combined casein was deposited. The liquor was allowed to stand for 24 hours. Further through processes of dehydration, drying and grinding, iodine-containing milkcasein was obtained.

Process for the preparation 5

Iodine-containing soybean-protein was obtained through the process similar to the Process 4, except that soybean protein was employed instead of milkcasein.

Process for the preparation 6

Iodine-containing corn-protein was obtained through the process similar to the Process 4, except that corn protein was employed instead of milkcasein.

Process for the preparation 7

Aqueous solution of sodium carbonate was added to 80 ml of pig serum to adjust the pH value to pH 9.4. To the liquor was gradually added under stirring a solution of 2.5 g of iodine and 3.3 g of potassium iodide in 200ml of water, and the liquor was allowed to stand at room temperature for 24 hours. Then the pH value was adjusted with 10% sulfuric acid to pH 5.0, 100 ml of ethanol was added thereto to deposit iodine-containing protein. It was dehydrated, dried and ground to give iodine-containing serum-protein.

Process for the preparation 8

A solution of 11 g of potassium iodide and 4.2 g of potassium iodate in 600 ml of water was added to 100 g of milkcasein and stirred. 4 ml of 12N hydrochloric acid was dropwise and gradually added thereto, over a period of 1 hour and stirred. The liquor was allowed to stand at room temperature for 24 hours. Further through processes of dehydration, drying and grinding, iodine-containing milkcasein was obtained.

Process for the preparation 9

A solution of 11 g of potassium iodide and 4.2 g of potassium iodate in 60 ml of water was added to 100 g of milkcasein, and kneaded therewith. The kneaded matter was dried and ground to give iodine-containing milkcasein.

Process for the preparation 10 (Comparison Example)

A solution of 14.5 g of potassium iodide in 60 ml of water was added to 100 g of milkcasein, and kneaded therewith. The kneaded matter was dried and ground to give iodine-containing milkcasein.

Process for the preparation 11 (Comparison Example)

A solution of 18.7 g of potassium iodate in 60 ml of water was added to 100 g of milkcasein, and kneaded therewith. The kneaded matter was dried and ground to give iodine-containing milkcasein.

In the below Table 1 are shown the total iodine amount, the amount of combined iodine, and the ratio between them (total iodine amount/combined iodine amount) of the iodine-containing protein obtained in the aforesaid Processes for the Preparation No. 1 to No. 11.

TABLE 1

| Process | Total iodine amount | Combined iodine amount | Total iodine amount/ Combined iodine amount |
|---|---|---|---|
| 1 | 8.6% | 1.2% | 7.2 |
| 2 | 12.0% | 3.8% | 3.2 |
| 3 | 19.0% | 8.5% | 2.2 |
| 4 | 4.8% | 3.8% | 1.3 |
| 5 | 1.9% | 1.0% | 1.9 |
| 6 | 4.1% | 3.1% | 1.3 |
| 7 | 4.5% | 4.3% | 1.0 |
| 8 | 9.5% | 3.7% | 2.6 |
| 9 | 9.3% | — | — |
| 10 | 9.8% | — | — |
| 11 | 9.7% | — | — |

*Combined iodine amount = Total iodine amount − iodine amount eluted in water

EXAMPLE 2

Time for supplying iodine-containing protein to broilers.

(Test conditions)

Feedstuff: Test feedstuff comprising principally corn and refined soybean protein, wherein CP ratio is 19% in the former period, and 15% in the latter period.

Blending ratio of the test material to the feedstuff: As the amount of combined-iodine, 35 ppm of the iodine-containing protein obtained in the Process 4 was added to the feedstuff.

Test section A (section for supplying the test material in the former period): The test material was supplied in the period of from the age of 9 days to 4 weeks, thereafter test-material-free feedstuff was fed till the age of 60 days.

Test section B (Section for supplying the test material in the latter period): Test material was supplied in the period of from the age of 5 weeks to 60 days, and the test material-free feedstuff was fed prior to that time.

Control section: The test-material-free feedstuff was fed.

Environment: In the latter period, the poultry were bred individually in respective cages in a room at the temperature of 22° to 25° C.

TABLE 2

|  | Section | n | Requirement rate*** | Abdominal fat (g) | White-meat weight (g) |
|---|---|---|---|---|---|
| Male | Control section | 10 | 2.19 | 25.3 ± 3.2 | 82.5 ± 4.2 |
|  | Section A | 10 | 2.21 | 27.1 ± 3.5 | 83.1 ± 6.5 |
|  | Section B | 10 | 2.11 | *21.2 ± 4.6 | **89.2 ± 5.2 |
| Female | Control Section | 10 | 2.35 | 42.6 ± 6.4 | 78.0 ± 3.8 |
|  | Section A | 9 | 2.36 | 40.3 ± 5.9 | 78.3 ± 6.1 |
|  | Section B | 10 | 2.28 | **26.2 ± 11.1 | 79.5 ± 5.4 |

*Significant difference of 5% risk from the control section
**Significant difference of 1% risk from the control section
***Requirement rate is calculated based on the data from the arrival of the chicken to the age of 60 days.

From the above test results, significant difference can be recognized in the white-meat weight of the male, and in the abdominal fat of the female respectively in the Section B, i.e. the section for supplying the test material in the latter period, and referring to the time for supplying the iodine-containing protein, effect of improving the meat quality can be recognized in the latter period supply.

EXAMPLE 3

Supply concentration of iodine-containing protein to broilers.

(Test conditions)

Feedstuff: Test feedstuff comprising principally corn and refined soybean protein, wherein 15% CP was contained.

Test period: From the age of 30 days to the age of 60 days

Blending ratio of the test material to the feedstuff: As the combined-iodine, the iodine-containing protein obtained in the Process 4 was added to the feedstuff at the following rates; none to the control, 3 ppm, 30 ppm, and 300 ppm.

Environment: The poultry were bred individually in cages in a room at the temperature of 22° to 25° C.

TABLE 3

|  | Section | n | Requirement rate | Abdominal fat (g) | White-meat weight (g) |
|---|---|---|---|---|---|
| Male | Control section | 10 | 2.21 | 28.3 ± 3.5 | 83.0 ± 3.5 |
|  | 3.0 PPM | 10 | 2.20 | 27.1 ± 2.6 | 85.1 ± 3.9 |
|  | 30 PPM | 10 | 2.14 | 25.9 ± 4.3 | *87.5 ± 4.2 |
|  | 300 PPM | 10 | 2.24 | **19.5 ± 7.6 | 84.2 ± 5.1 |
| Female | Control section | 10 | 2.35 | 50.2 ± 8.3 | 80.0 ± 4.3 |
|  | 3.0 PPM | 10 | 2.34 | 49.3 ± 5.1 | 78.5 ± 6.1 |
|  | 30 PPM | 10 | 2.31 | **31.2 ± 9.5 | 83.2 ± 8.2 |
|  | 300 PPM | 10 | 2.37 | **24.5 ± 12.0 | 81.4 ± 3.7 |

*Significant difference of 5% risk from the control section
**Significant difference of 1% risk from the control section From the above test results it can be recognized that in the case of supplying at least 3 ppm of the iodine-containing protein as the amount of the combined iodine, the supply has a good effect of improving the meat quality, as compared with the result of the control section.

EXAMPLE 4

Effect of the protein containing iodide and iodate.
(Test conditions)
Test method: Similar to the Example 3
Test section:
Section A—0.1% of the iodine-containing protein obtained in the Process 8 was added.
Section B—0.1% of the iodine-containing protein obtained in the Process 9 was added.
Section C—0.1% of the iodine-containing protein obtained in the Process 10 was added.
Section D—0.1% of the iodine-containing protein obtained in the Process 11 was added.

TABLE 4

|  | Section | n | Requirement rate | Abdominal fat (g) | White-meat weight (g) |
|---|---|---|---|---|---|
| Male | Control Section | 10 | 2.28 | 32.3 ± 4.1 | 83.1 ± 5.1 |
|  | Section A | 10 | 2.19 | 30.2 ± 3.2 | *87.3 ± 3.6 |
|  | Section B | 10 | 2.22 | 29.9 ± 5.2 | 86.2 ± 4.2 |
|  | Section C | 10 | 2.29 | 35.6 ± 7.1 | 80.8 ± 4.5 |
|  | Section D | 10 | 2.28 | 34.3 ± 4.7 | 81.6 ± 6.3 |
| Female | Control section | 10 | 2.32 | 63.1 ± 6.2 | 80.3 ± 4.5 |
|  | Section A | 10 | 2.29 | **50.3 ± 4.9 | 84.6 ± 6.1 |
|  | Section B | 10 | 2.30 | *55.6 ± 7.1 | 83.4 ± 3.5 |
|  | Section C | 10 | 2.31 | 60.1 ± 8.0 | 79.0 ± 5.2 |
|  | Section D | 10 | 2.30 | 67.3 ± 6.5 | 79.2 ± 4.8 |

*Significant difference of 5% risk from the control section
**Significant difference of 1% risk from the control section According to the above test result, effect attained in the Section A and Section B are substantially the same. In the Section C and Section D, as compared with the control section, any noticeable effect of improving the meat quality can not be recognized.

EXAMPLE 5

The iodine-containing protein obtained in the Process 4 was added to the broiler feedstuff to be fed in the latter period and in the finishing time, and it was supplied to breed the poultry starting from the age of 30 days till the age of 60 days. Incidentally the additive concentration was determined in terms of the combined-iodine, and the number of the broilers were 800 per section.

TABLE 5

| | (i) Summertime (July–September) | | | | | |
|---|---|---|---|---|---|---|
| | Average weight of a broiler | | | | | |
| Test sections | Dark meat Breast meat White meat | Wing root Wing tip | Liver Heart Muscular stomach | Fat Skin Tail | Average per broiler Body weight | Average per broiler Feedstuff consumption |
| Control section (Additive-free) | 1,002g | 195g | 84g | 160g | 2,635g | 6,219g |
| Section A (10 ppm addition) | 1,029 | 206 | 84 | 152 | 2,644 | 6,266 |
| Section B (35 ppm addition) | 1.039 | 208 | 85 | 151 | 2,662 | 6,309 |

TABLE 6

| | (ii) Autumntime (October–December) | | | | | |
|---|---|---|---|---|---|---|
| | Average weight of a broiler | | | | | |
| Test sections | Dark meat Breast meat White meat | Wing root Wing tip | Liver Heart Muscular stomach | Fat Skin Tail | Average per broiler Body weight | Average per broiler Feedstuff consumption |
| Control section (Additive-free) | 1,141g | 217g | 80g | 178g | 2,926g | 6,762g |
| Section A (10 ppm addition) | 1,168 | 223 | 90 | 176 | 2,981 | 6,800 |
| Section B (17.5 ppm addition) | 1,154 | 220 | 86 | 181 | 2,938 | 6,690 |
| Section C (25 ppm addition) | 1,152 | 220 | 91 | 180 | 2,966 | 6,804 |

EXAMPLE 6

0.03% of the iodine-containing protein obtained in the Process 9 was added respectively to the broiler feedstuff for each test period. Incidentally the number of the broiler were 800 per section.

TABLE 7

| | (i) Wintertime (January–March) | | | | | |
|---|---|---|---|---|---|---|
| | Average weight of a broiler | | | | | |
| Test sections | Dark meat Breast meat White meat | Wing root Wing tip | Liver Heart Muscular stomach | Fat Skin Tail | Average per broiler Body weight | Average per broiler Feedstuff consumption |
| Control section (Additive-free) | 1,125g | 218g | 103g | 191g | 2,852g | 6,609g |
| Section A (Supplied through the entire period) | 1,125 | 215 | 100 | 208 | 2,845 | 6,838 |
| Section B (Supplied from the age of 30 days to the shipment) | 1,138 | 213 | 101 | 177 | 2,856 | 6,656 |
| Section C (Stopped supply 1 week before shipment) | 1,138 | 217 | 105 | 195 | 2,868 | 6,611 |

TABLE 8

| | (ii) Summertime (July–September) | | | | | |
|---|---|---|---|---|---|---|
| | Average weight of a broiler | | | | | |
| Test sections | Dark meat Breast meat White meat | Wing root Wing tip | Liver Heart Muscular stomach | Fat Skin Tail | Average per broiler Body weight | Average per broiler Feedstuff consumption |
| Control section (Additive-free) | 1,082g | 205g | 84g | 164g | 2,741g | 6,048g |
| Section A (Supplied through the entire period) | 1,075 | 220 | 86 | 165 | 2,745 | 6,139 |
| Section B (Supplied from the age of 30 days to the shipment) | 1,089 | 221 | 85 | 162 | 2,717 | 6,050 |
| Section C (Stopped supply | 1,107 | 219 | 87 | 169 | 2,754 | 6,061 |

TABLE 8-continued

| | (ii) Summertime (July–September) | | | | | |
|---|---|---|---|---|---|---|
| | Average weight of a broiler | | | | | |
| Test sections | Dark meat Breast meat White meat | Wing root Wing tip | Liver Heart Muscular stomach | Fat Skin Tail | Average per broiler Body weight | Average per broiler Feedstuff consumption |
| 1 week before shipment) | | | | | | |

We claim:

1. Method of breeding poultry for food characterized by feeding feedstuff that contains iodide-and-iodate-containing protein or a reaction product of iodine with a protein to the poultry for food at the age of from 10 to 60 days.

2. Method of breeding poultry as claimed in claim 1, characterized by feeding feedstuff that contains the iodide-and-iodate-containing protein in the manner that the iodine concentration is from 1 to 3500 ppm.

3. Method of breeding poultry as claimed in claim 1, characterized by feeding feedstuff that contains the reaction product of iodine with a protein in the manner that the iodine concentration is from 1 to 350 ppm.

* * * * *

UNITED STATES PATENT AND TRADEMARK OFFICE
CERTIFICATE OF CORRECTION

PATENT NO. : 4,858,560

DATED : August 22, 1989

INVENTOR(S) : Kunicki Hayashi, et al

It is certified that error appears in the above-identified patent and that said Letters Patent is hereby corrected as shown below:

The Foreign Application Priority Data was omitted.
It should appear as follows:

-- [30]　　　　Foreign Application Priority Data

Jan. 7, 1987 [JP]　Japan ................62-1513 --

Signed and Sealed this

Twenty-sixth Day of June, 1990

*Attest:*

HARRY F. MANBECK, JR.

*Attesting Officer*　　　　*Commissioner of Patents and Trademarks*